United States Patent [19]

Pope et al.

[11] Patent Number: 5,377,100
[45] Date of Patent: Dec. 27, 1994

[54] METHOD OF ENCOURAGING ATTENTION BY CORRELATING VIDEO GAME DIFFICULTY WITH ATTENTION LEVEL

[75] Inventors: Alan T. Pope, Poquoson; Edward H. Bogart, Hampton, both of Va.

[73] Assignee: The United States of America as represented by the Administrator of the National Aeronautics and Space Administration, Washington, D.C.

[21] Appl. No.: 29,808
[22] Filed: Mar. 8, 1993
[51] Int. Cl.$^5$ .............................................. G06F 15/44
[52] U.S. Cl. .................................................. 364/410
[58] Field of Search ............ 364/410, 411, 412, 413.05, 364/413.04, 413.03, 413.02; 128/731, 732; 273/438, 434

[56] References Cited

U.S. PATENT DOCUMENTS

| | | |
|---|---|---|
| 3,877,466 | 4/1975 | Montor . |
| 3,890,957 | 6/1975 | Freeman . |
| 3,896,790 | 7/1975 | Dikmen . |
| 4,008,714 | 2/1977 | Silva et al. . |
| 4,031,883 | 6/1977 | Fehmi et al. . |
| 4,136,684 | 1/1979 | Scattergood et al. . |
| 4,188,956 | 2/1980 | John ..................................... 128/731 |
| 4,203,452 | 5/1980 | Cohen . |
| 4,228,807 | 10/1980 | Yagi et al. . |
| 4,279,258 | 7/1981 | John ..................................... 128/731 |
| 4,332,566 | 6/1982 | Mazeski et al. . |
| 4,334,545 | 6/1982 | Shiga . |
| 4,354,505 | 10/1982 | Shiga . |
| 4,461,301 | 7/1984 | Ochs . |
| 4,503,863 | 3/1985 | Katims . |
| 4,632,126 | 12/1986 | Aguilar . |
| 4,683,891 | 8/1987 | Cornellier et al. ................... 128/630 |
| 4,800,893 | 1/1989 | Ross et al. . |
| 4,883,067 | 11/1989 | Knispel et al. . |
| 4,919,143 | 4/1990 | Ayers ................................. 128/732 |
| 4,928,704 | 5/1990 | Hardt . |
| 4,987,903 | 1/1991 | Keppel et al. . |
| 5,001,632 | 3/1991 | Hall-Tipping . |
| 5,213,338 | 5/1993 | Brotz ................................. 273/460 |

OTHER PUBLICATIONS

Excerpt from "NASA's Innovators", NASA Tech Briefs, Aug. 1991, p. 12.
J. F. Lubar, "Discourse on the development of EEG diagnostics and biofeedback for attention-deficit/-hyperactivity disorders", Biofeedback and Self-Regulation, vol. 16, No. 3, 1191, pp. 201–225.
B. Strietberg, et al., "COMSTAT rule for vigilance classification based on spontaneous EEG activity", Neuropsychobiology, 17, 1987, pp. 105–117.
"Undifferentiated attention-deficit disorder", American Psychiatric Association: Diagnostic and Statistical Manual of Mental Disorders, 3rd Ed. Rev., Washington, DC: APA, m1987, pp. 95–99.
S. A. Ciarcia, "Computers on the brain, Part 1," BYTE, Jun. 1988, pp. 273–285.
S. A. Ciarcia, "Computers on the brain, Part 2," BYTE, Jul. 1988, pp. 289–296.
H. Schwilden et al., "Closed-loop feedback control of propofol anaesthesia by quantititative EEG analysis in humans", Br. J. Anaesth., 1989, 62, pp. 290–296.
Ruth J. Arnegard et al., "Multi-attribute task battery: Applications in pilot workload and srategic behavior researvh", Paper presented at the Sixth International Symposium on Aiation Psychology, Columbus, Ohio, Apr. 29–May 2, 1991.
C. S. Carver et al., "Attention and self-regulation: A control-theory approach to human behavior", SSSP, Springer–Verlag, NY, 1981, pp. 34–35.
T. B. Mulholland, "Training visual attention, Academic Therapy," vol. X, No. 1, 1974, pp. 5–17.

*Primary Examiner*—Donald E. McElheny, Jr.
*Attorney, Agent, or Firm*—Linda B. B. Blackburn

[57] ABSTRACT

A method of encouraging attention in persons such as those suffering from Attention Deficit Disorder is provided by correlating the level of difficulty of a video game with the level of attention in a subject. A video game comprises a video display which depicts objects for interaction with a player and a difficulty adjuster which increases the difficulty level, e.g., action speed and/or evasiveness of the depicted object, in a predetermined manner. The electrical activity of the brain is measured at selected sites to determine levels of awareness, e.g., activity in the beta, theta, and alpha states. A value is generated based on this measured electrical signal which is indicative of the level of awareness. The difficulty level of the game is increased as the awareness level value decreases and is decreased as this awareness level value increases.

14 Claims, 6 Drawing Sheets

METHOD OF ENCOURAGING ATTENTION BY CORRELATING VIDEO GAME DIFFICULTY WITH ATTENTION LEVEL

ORIGIN OF THE INVENTION

The invention described herein was jointly made by an employee of the United States Government and by a contractor employee in the performance of work under a NASA contract and is subject to provisions of Section 305 of the National Aeronautics and Space Act of 1958, as amended, Public Law 85-568 (72 Stat. 435; 42 USC 2457). cl BACKGROUND OF THE INVENTION

1. Field of the Invention

The present invention relates generally to using biofeedback to modify behavior and more specifically to a method of altering the level of difficulty of an electronic game in response to measured attention levels of the player, whereby the player learns to increase his attention to overcome the effects of such conditions such as Attention Deficit Disorder.

2. Related Art

Attention Deficit Disorder (ADD) is a behavioral disorder characterized by the inability to sustain attention long enough to perform activities such as schoolwork or organized play. Current treatments for ADD include medication and brainwave biofeedback training. In biofeedback training, the trainee, usually a child, is provided information in the form of a conventionally produced electroencephalograph (EEG) display which shows him how well he is producing the brainwave pattern(s) indicative of attention. This feedback consists of a video representation or paper hard copy of the EEG graph. The procedure, though providing useful information, is very routine and predictable, and accordingly induces boredom. Positive reinforcement of attention states is accordingly difficult to obtain, especially in children, and more especially in children exhibiting ADD.

The management of attention is important for success in a wide range of endeavors from sport to study. The ability to remain aware of fluctuating attentional states, the ability to maintain effective states and the ability to recover efficiently from attention lapses are valuable in task settings requiring recognition and response.

Several U.S. patents propose biofeedback systems to monitor and/or improve mental states. For example, U.S. Pat. No. 3,877,466 to Montor discloses an attention level analyzer which comprises an EEG instrument attached to a subject. When the EEG output is in the inattentive band of 8-13 Hz, a clock is actuated which in time will activate a tone generator and another clock, and so on until a monitor is alerted when the attention has lapsed for an unacceptable period of time.

U.S. Pat. No. 4,008,714 to Silva et al. describes a system which generates an audible indication and starts a prerecorded educational program upon determination that the subject has a sufficient concentration level.

U.S. Pat. No. 4,461,301 to Ochs discloses a biofeedback system which provides a visual display of a metric indication of a physiological function and a visual display of a target metric which is readjusted to prevent attainment of the target.

U.S. Pat. No. 4,883,067 to Knispel et al. discloses an apparatus which derives a subject's EEG signal, converts the signal into music via a synthesizer, and plays the generated music back to the subject to close the biofeedback loop.

OBJECTS

It is accordingly an object of the present invention to provide a method and apparatus which reinforces attention states.

It is another object of the present invention to reinforce attention states in persons affected by Attention Deficit Disorder.

It is a further object of the present invention to reinforce attention states in children, especially in children affected by Attention Deficit Disorder.

It is another object of the present invention to maintain attention levels once obtained in a subject.

It is a further object of the present invention to achieve the foregoing objects while providing entertainment to the subject to maintain the attention level.

It is yet another object of the present invention to achieve the foregoing objects in a cost-efficient, straightforward manner.

Additional objects and advantages of the present invention are described below.

SUMMARY OF THE INVENTION

The foregoing and additional objects are obtained by a method of encouraging attention by correlating video game difficulty with attention level according to the present invention. A conventional video game comprises a video display which depicts objects for interaction with a player and a difficulty adjuster which increases the difficulty level, e.g., action speed and/or evasiveness of the depicted object, in a predetermined manner. The electrical activity of the brain is measured at selected sites to determine levels of awareness, e.g., activity in the beta, theta, and alpha frequency bands. A value is generated based on this measured electrical signal which is indicative of the level of awareness. The difficulty level of the game is increased as the awareness level value decreases and is decreased as this awareness level value increases.

DETAILED DESCRIPTION OF THE INVENTION

Figure 1:
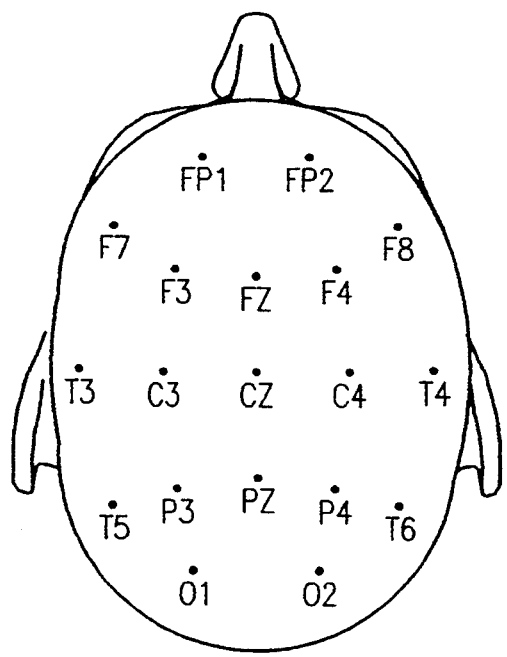
FIG. 1 is a top view of a human scalp showing conventional electrode sites for measuring EEG activity.

The management of attention is important for success in a wide range of endeavors from sport to study. The ability to remain aware of fluctuating attentional states, the ability to maintain effective states, and the ability to recover efficiently from attention lapses are valuable in task settings requiring recognition and response. In addition to personal differences in these abilities, there are also differences in the nature of tasks that either foster or discourage effective attention. As automated systems become more capable, human operators spend less time actively controlling such systems and more time passively monitoring system functioning. This type of task demand challenges human capability for sustained attention.

Attention may be usefully characterized by three aspects: (1) distribution (diffused versus concentrated); (2) intensiveness (alert versus inattentive); and (3) selectivity (the "what" of attention). See, *Attention and Self-Regulation: A Control Theory Approach to Human Behavior*, C. S. Carver and M. F. Scheier, Springer-Verlag, New York, 1981, pp. 34-5. Distribution and intensiveness are influenced by the state of awareness being experienced, and selectivity refers to the contents of awareness. In designing for effective integration of human and system, it is important to provide ready access to useful information so that the contents of awareness support informed action. It is also important to design for human involvement in system function to promote effective states of awareness, i.e., to promote consistent mental engagement in the supervisory task. Mental engagement in automated environments may be enhanced by judicious allocation of task responsibility between the human and the automated system.

The electroencephalogram (EEG) or brainwave has long been used to index states of consciousness or awareness. Stages of sleep are readily mapped by analyzing the frequency content of the electrical activity of the brain. Less well studied are the stages of waking consciousness. However, recent work has identified characteristic patterns in three established brainwave frequency bands that distinguish among various states of attention. Relatively greater beta (approximately 13–20 Hz) activity has been observed for vigilant states, whereas alpha (approximately 8–13 Hz) activity predominates in alert but less mentally busy states, and theta (approximately 4–8 Hz) activity rises as attention lapses. This beta state is sometimes defined as beta$_1$, and a beta$_2$ state is defined from 20–40 Hz. See "COMSTAT Rule for Vigilance Classification Based on Spontaneous EEG Activity," B. Streitberg et al., *Neuropsychobiology*, Vol. 17, 1987, pp. 105-17. These brainwave-state correspondences have proven useful in assessing attention-related disorders as described below. See "Discourse on the Development of EEG Diagnostics and Biofeedback for Attention Deficit/Hyperactivity Disorders," J. F. Lubar, *Biofeedback and Self-Regulation.*, Vol. 16, No. 13, 1991, pp. 201-25. However, within these guidelines there are significant individual differences. The set of frequency bands and recording sites that discriminate best among states of awareness for one individual are not likely to be the same set for another. Therefore, to derive an EEG index of attention with which to assess mental engagement in a task, it is necessary to develop each subject's personalized EEG-to-state mapping profile.

Figure 2:
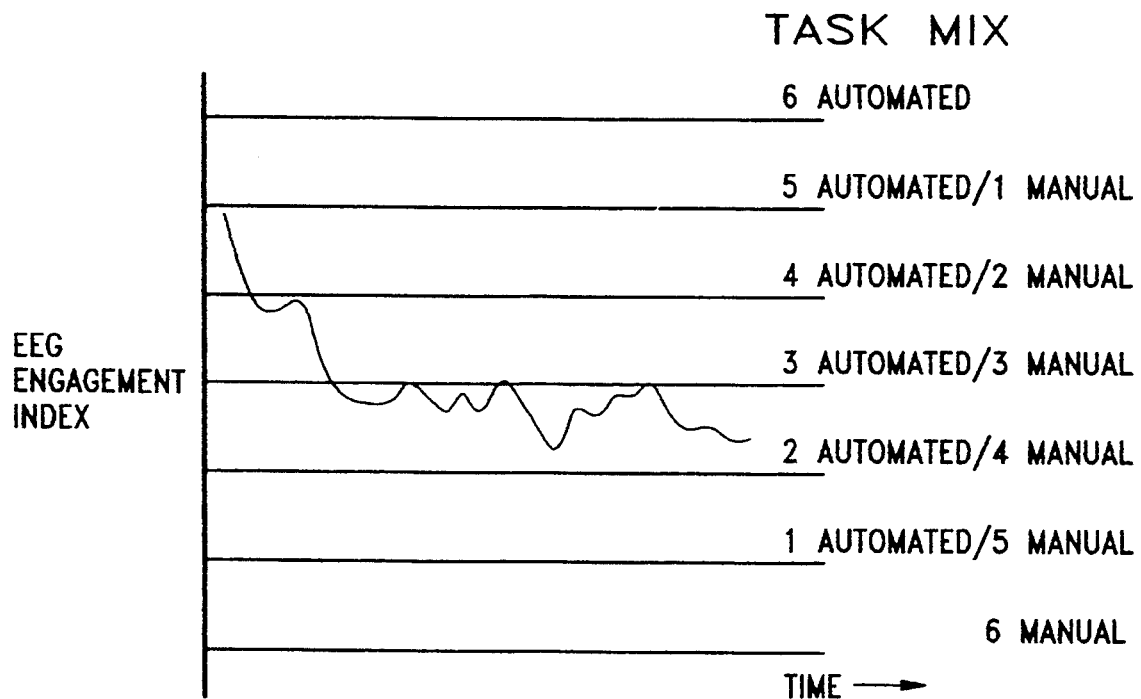
FIG. 2 graphs the EEG engagement index versus time for a sample test battery comprising a variety of manual/automated mixes.

This profiling procedure is conducted in a prescribed task environment. The procedure involves recording topographical EEG data from nineteen electrode sites while a subject performs the test battery. These conventional electrode sites are depicted in FIG. 1. A methodology and system have been developed to support the determination of optimal human (manual)/system (automated) task allocation "mixes" based upon a brain activity criterion of consistent mental engagement, as depicted in FIG. 2. In this methodology, an experimental subject interacts with a set of tasks presented on a desktop computer display while the subject's electrical brain activity is monitored via a conventional EEG system.

This evaluation methodology has been developed in the context of computer-assisted flight management. The tasks in the set, or Multi-Attribute Task (MAT) Battery, are designed to be analogous to tasks that crew members perform in flight management. The MAT Battery Video display is composed of four separate task areas, or windows, comprising the monitoring, tracking, communication, and resource management tasks. Each task may be fully or partially automated. The monitoring subtask requires a subject to detect warning light changes and scale pointer offsets. When this subtask is automated, these events are responded to by the computer. The compensatory tracking task requires a subject to keep a moving symbol within a central rectangle. This task is automated by constraining movement of the symbol in one or both axes to within the central rectangle. The communications task requires a subject to discriminate an auditory message intended for his flight from other messages and to follow the message command to set radio frequencies. When this subtask is automated, the frequencies are set automatically when the message is received. The resource management subtask is presented to subjects as a fuel management task. A subject is required to maintain a prescribed level in each of two tanks by controlling pumps from reservoirs. The computer maintains the levels when the task is automated. This battery is described more fully in "Multi-Attribute Test Battery: Applications in Pilot Workload and Strategic Behavior Research," R. J. Arnegard and J. R. Comstock, *Proceedings of the Sixth International Symposium on Aviation Psychology*, presented in Columbus, Ohio, 1991, pp. 1118-1123.

The level of automation of the task battery may then be varied so that all, none, or a subset of the system control functions require subject intervention. This variable automation feature enables a range of levels of demand for operator involvement in system management to be imposed. Corresponding to these levels of involvement are degrees of mental engagement that are often spoken of in terms of being "in" or "out of the loop". Mental engagement in an automated task may not be sufficient to promote an effective state of awareness. Monitoring brain activity provides a window through which to view the states of a subject in this situation. The MAT is systematically stepped through its range of automation levels. At each step, a spatial map of EEG activity is generated for each of the alpha, beta, and theta frequency bands that portrays the scalp distribution of activity within that band. In this way, a trio of brainmaps is generated that corresponds to the state experienced at each level of task automation. The EEG data represented in the entire set of brainmaps are used to derive state discriminant functions for the subject.

Once an individual subject's characteristic mapping profile has been determined using the above described MAT battery or any other suitable mapping procedure, an index is constructed according to the present invention which is designed to be maximally sensitive to changes in state. The mapping procedure for children should be similar with tailoring to a child's normal or deficient attention abilities. The index has the form:

$$(K_1 * bS_1)/(K_2 * aS_2 + K_3 * tS_3)$$

where
  $bS_1$ = beta activity at electrode site 1
  $aS_2$ = alpha activity at electrode site 2
  $tS_3$ = theta activity at electrode site 3
with $S_1$, $S_2$, and $S_3$ representing the sites at which the activity sites at which the activity in the associated band is most discriminating among states, i.e., each selected site has the most activity in one band for one of the three states. $K_1$, $K_2$ and $K_3$ are coefficient weights that reflect the relative contributions that the three band/site factors made to the mental activity discrimination. This index is constructed to have higher values for subject states corresponding to greater degrees of mental engagement; i.e., greater demands for operator involvement, and is thus awareness state sensitive.

In conventional pilot applications. the engagement index is next employed with the MAT or other test battery in a closed-loop control paradigm to observe the effects of adaptively allocating task responsibility between operator and automated system. That is, the task battery is adapted to the subject's degree of engagement in the task by assigning an additional subtask to the subject when it is determined that task engagement is waning over a time interval. Conversely, when the engagement index exhibits a sustained rise, indicating that the subject is capable of monitoring attentively, an additional battery subtask is automated. In this way, the feedback system eventually achieves a steady-state condition in which neither sustained rises nor sustained declines in the engagement index are observed. The combination of automated and manual subtasks, the task "mix," that the subject is presented in this condition may be considered optimal by the criterion of mental engagement reflected in the EEG state index. This adaptive process is essentially a feedback control process whereby the reference EEG condition, stable short-cycle oscillation of the engagement index, is achieved by systematic adjustment of task demand for operator participation. The conventional adaptive system is designed to evaluate automated task environments to determine the requirements for operator involvement that promote effective operator awareness states.

Symptoms of pure Attention-deficit Disorder (ADD)-short attention span and poor focusing and concentration skills-are present in a majority of children who are hyperkinetic, or who have a specific learning disorder or who exhibit a conduct disorder. Lubar and coworkers in the previously discussed article have found that topographic brain mapping of EEG frequency bands discriminate between children classified as pure ADD and matched controls, and that the discriminations are stronger during task performance than during baseline conditions. ADD children showed greater increases in theta activity and decreases in beta activity during tasks. These findings strengthened the rationale for providing EEG biofeedback training to reverse these brain activity trends and improve attentional abilities.

Training is conventionally accomplished by providing the subject with a real-time display of the levels of beta and theta activity being produced. The display serves as both information and reward for the child's efforts to reduce theta activity and increase beta activity. Success at producing the desired brain activity changes as well as improvements in psychometric performance have been reported by Lubar as outcomes of training. However, the graphical or numerical display of the state activity is unexciting and further compounds inattention. Mulholland described a system for visual attention training using alpha activity as the control variable. See "Training Visual Attention," T. B. Mulholland, *Academic Therapy*, Vol 10, No. 1, 1974, pp. 5–17. Lubar specifically recommends the use of theta/beta and alpha/beta ratios as sensitive discriminators of ADD. The present invention uses brain activity band ratios in a training protocol that also employs the adaptive task concept.

The mission of achieving uneventful flight or observing graphical representations of attention level is not likely to interest a child for any meaningful period of time. Few activities can capture a child's attention like the exciting challenge of a video game. A wide variety of extremely popular video games capture the attention of children and adults with constantly changing images, exotic locales, quick action and difficult challenges. The present invention unites the popularity of video games with a biofeedback system to promote attention in the subject. The following is a non-limiting, illustrative example of the present invention.

Figure 4:
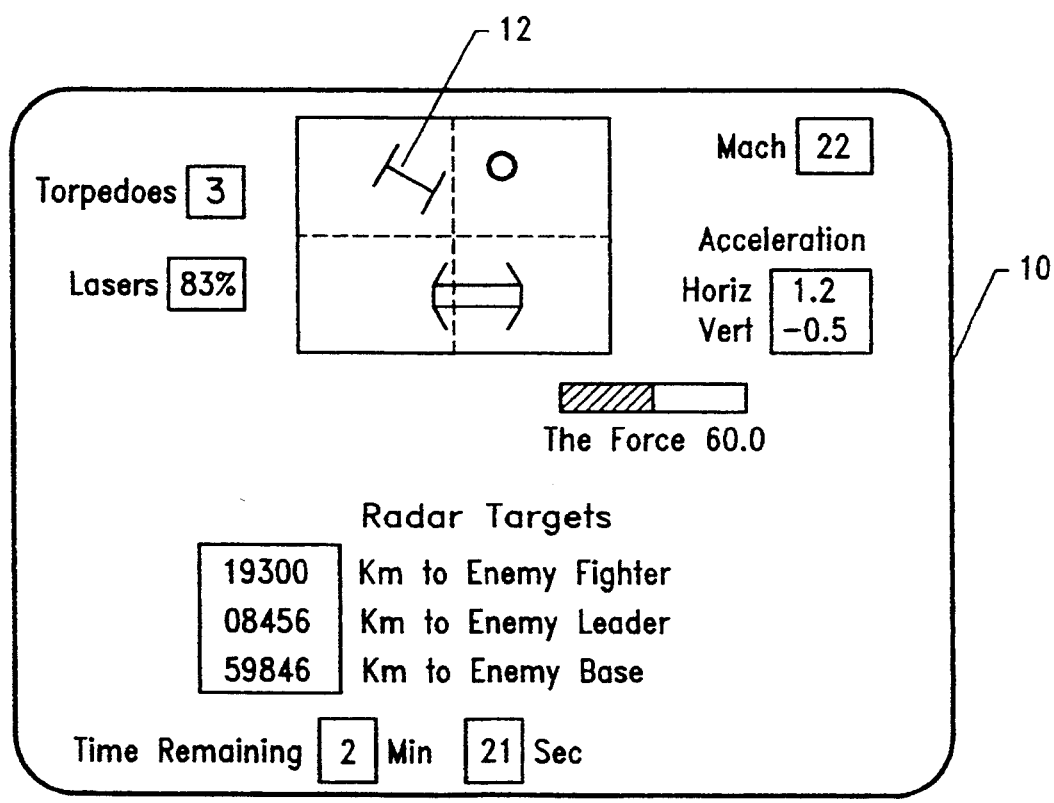
FIG. 4 is a front view of a sample video display generated according to the present invention.
Figure 5:
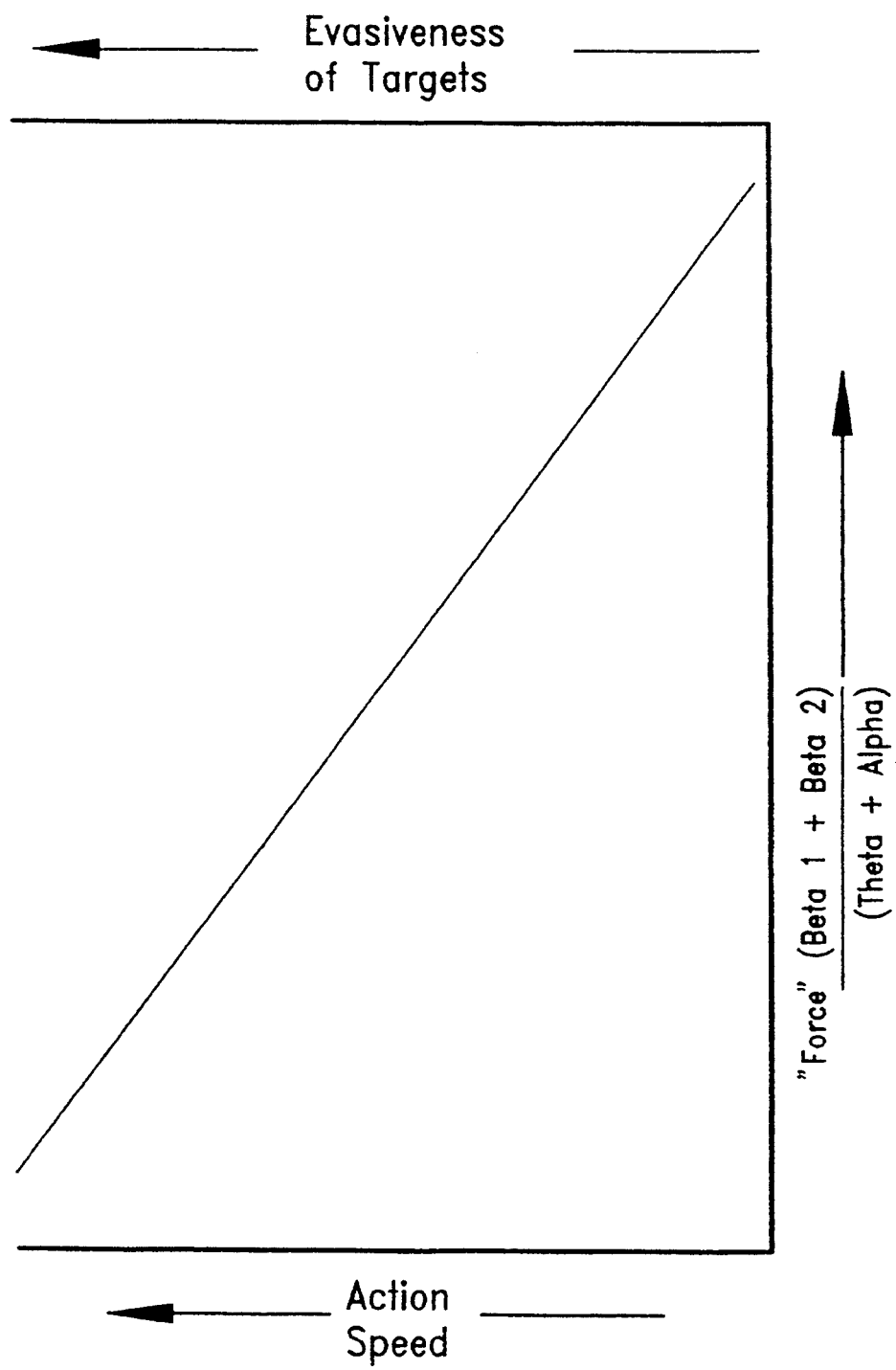
FIG. 5 graphs the general inverse relationship of a "force" indicative of awareness level versus game difficulty, specifically action speed and target evasiveness.

A video game program entitled "Star Pilot Game" was selected from a computer bulletin board. The program was modified as discussed below and a copy of the modified program implementing an embodiment of the method according to the present invention is enclosed per §608.05 of the MPEP. The video game program was written in BASIC and produces video images on a video monitor 10 shown in FIG. 3 and in greater detail in FIG. 4. More specifically, the program directs the video monitor 10 to produce target object images 12 such as enemy ships and bases of various shapes and point values as well as various information displays regarding such factors as speed, horizontal and vertical acceleration, amounts of remaining torpedoes and laser power, distance to the enemy ships, and the time remaining in the game. The normal object of such games is to destroy enemy ships without being destroyed, thereby accumulating points and in some instances advancing to the next level of the game. The player operates a joystick or mouse which permits him to move "his" ship on the video screen to avoid being hit by enemy firings and permits him to fire at the enemy objects. In many games, the program increases the difficulty of the game as a function of passing time and/or points accumulated and/or the proficiency level achieved. Another variable of difficulty is the skill level selected by the player at the outset of the game, e.g., "Beginner", "Intermediate", "Expert", etc. which serves as a starting point for subsequent increases in difficulty. As the difficulty level increases, the enemy ships move faster and/or move erratically, enemy ships fire more often, more enemy ships attack, the player's own firings must become more accurate as the "effective zone" of the firing decreases, etc. Numerous other operating functions can be altered to make the game more difficult. FIG. 5 graphs the general inverse relationship of the selected difficulty parameters of actions, speed and target evasiveness versus mental awareness level. This so-called "difficulty adjuster" is either implemented by software or hand-wired into the video game circuitry.

The present invention correlates the mental awareness level of a subject with the level of difficulty of the game. It should be noted that the following example employing a video monitor and personal computer is for purposes of illustration and is non-limiting. The present invention is applicable to portable electronic video games using discs or other storage media as well as other video game configurations.

Figure 3:
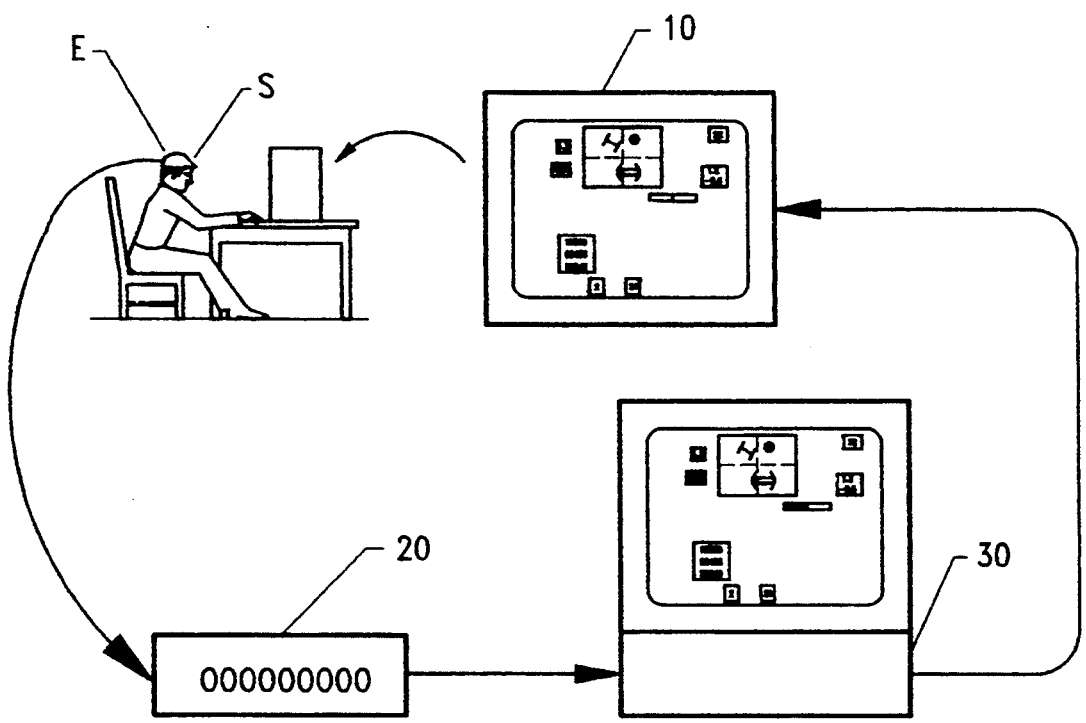
FIG. 3 is a schematic of the system according to the present invention.

Prior to playing the game, the subject performs a series of tasks such as those described above in reference to FIG. 1 in order to obtain the most active site for beta, alpha and theta activity. Once these three sites are identified, electrodes are always located there to detect the most active sites. As shown in FIG. 3, the subject S is seated to view a video monitor 10. Three electrodes E are attached to his scalp at the identified sites $S_1$, $S_2$ and $S_3$. The electrical signals indicative of mental activity are transmitted to an EEG interface 20 and then transmitted to a feedback controller 30 such as a personal computer which executes the program described below.

A particular system useful in the present invention as the EEG interface is the Hemispheric Activation Level Detector (HAL) described in greater detail in "Computers on the Brain, Part 1" by S. A. Ciarcia, Byte, June 1988, pp. 273-284. Basically, HAL incorporates a band-pass filter for filtering out undesired frequencies not in the range of 4-20 Hz, or 4-40 Hz if $beta_2$ is observed; a preamplifier for amplifying the filtered signals; an analog/digital converter for converting these filtered and amplified analog signals to digital signals for computer processing; and a control program for performing a Fast Fourier Transform on these digital signals.

Figure 6A:
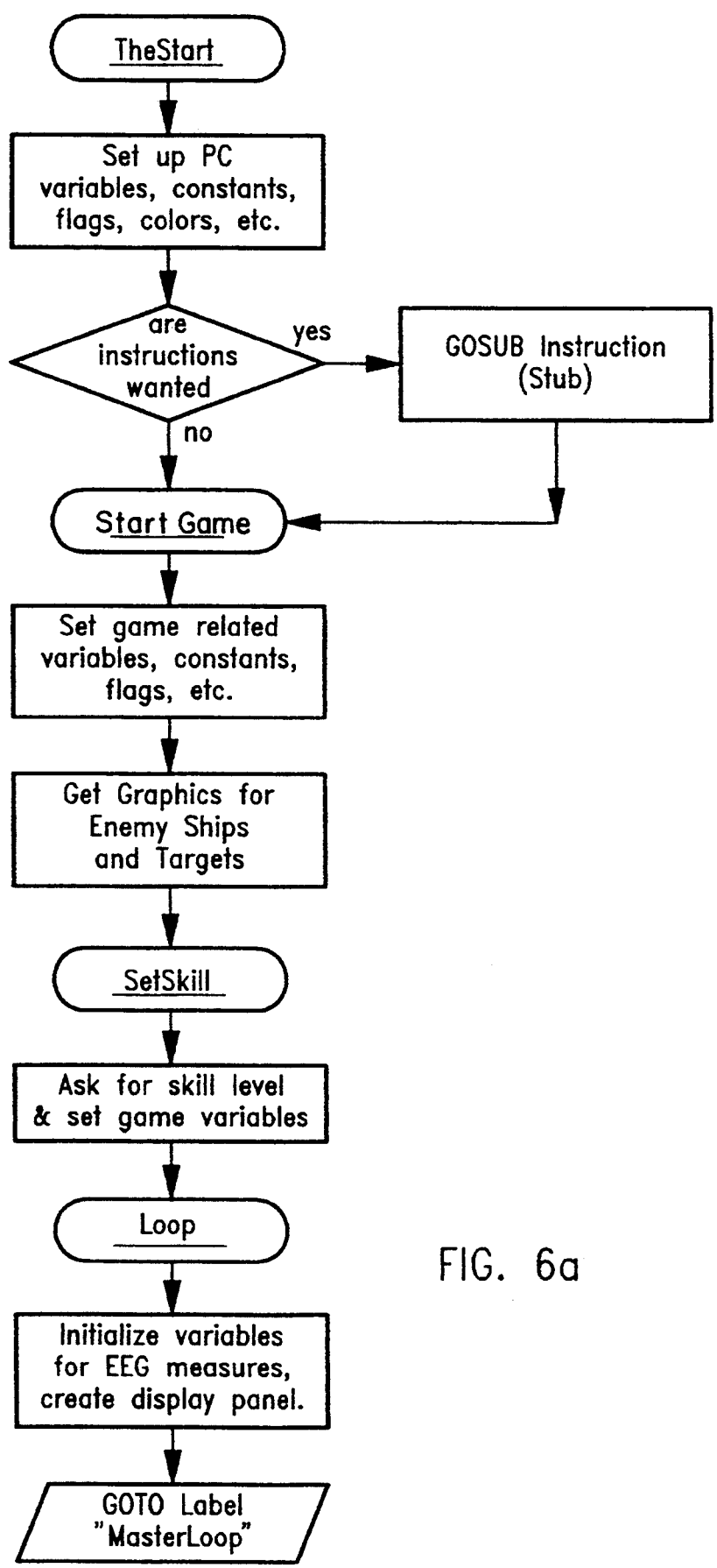
FIG. 6a–c are flow charts for implementing the present invention via a computer program.
Figure 6B:
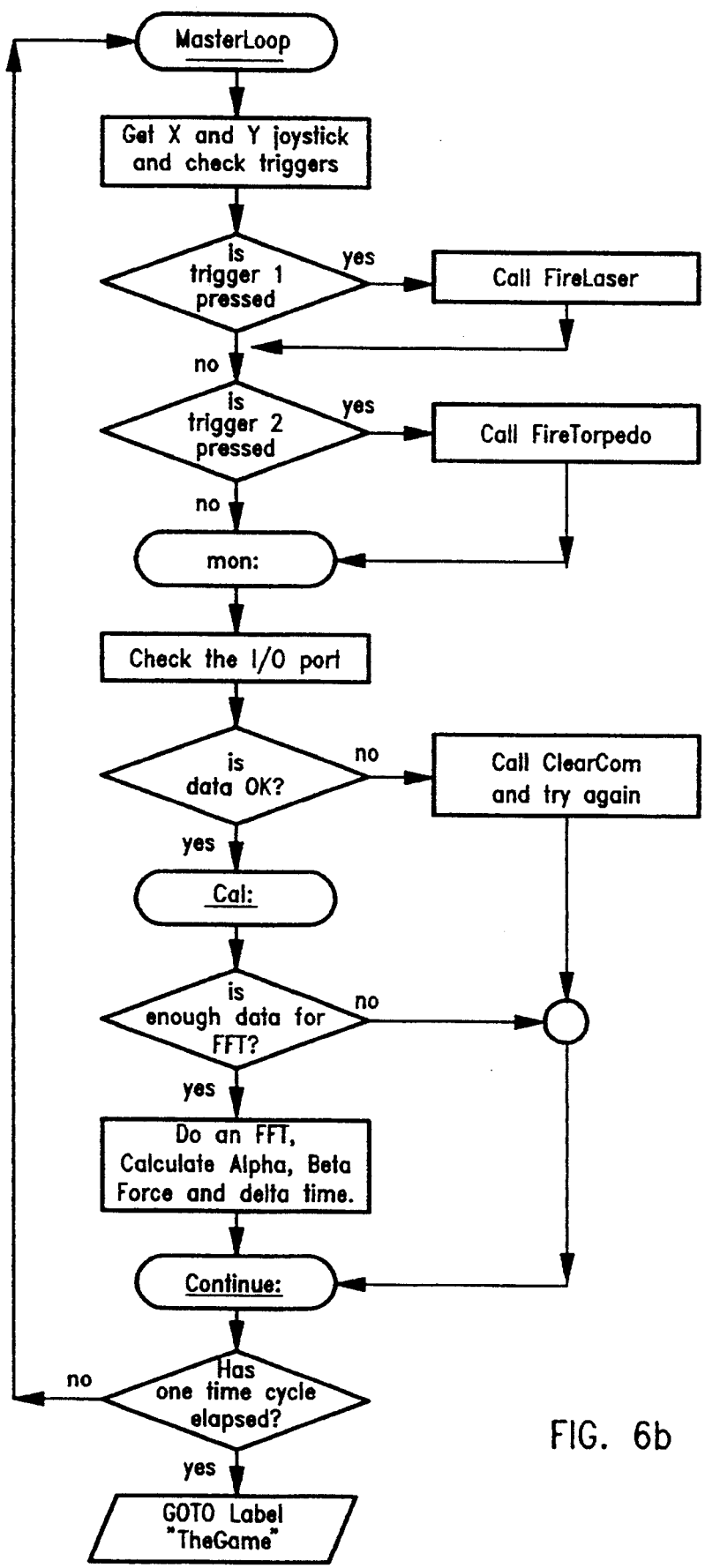
Figure 6C:
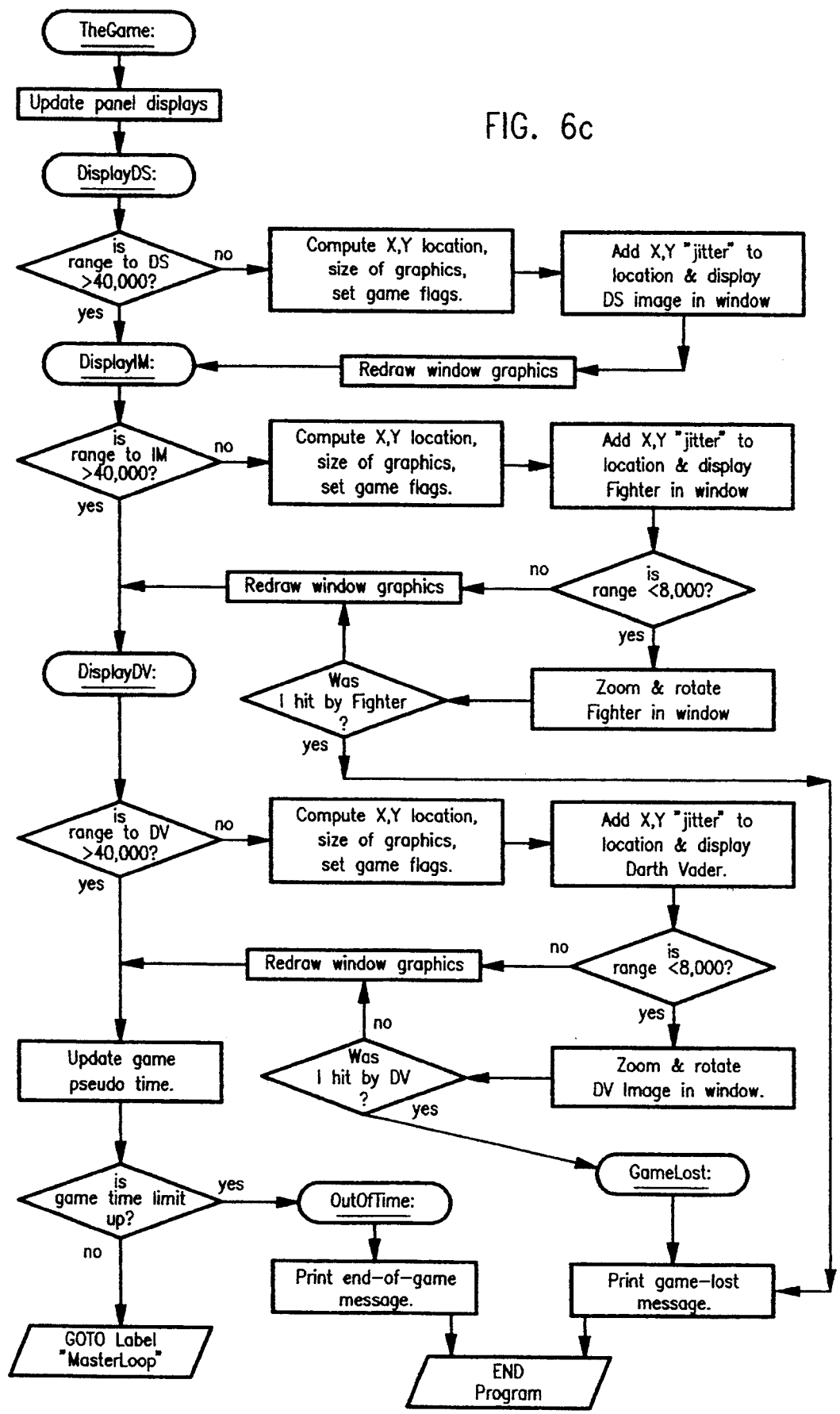

FIGS. 6a-c are flow charts outlining the software implemented steps of the invention. Of course the logic could be hardwired into circuitry. FIG. 6a shows a flow chart for the initialization portion of the video game. Operating instructions are provided if desired, the skill setting is determined by the operator and the EEG measures are initialized. Once completed, the game begins with attacking ships which the subject engages by, e.g., firing simulated lasers or torpedoes. During this segment, the software queries whether enough data is available from the electrodes and EEG interface to perform a Fast Fourier Transform (FFT). The FFT breaks down the wave generated by the electrode into simple sinusoidal components which make up the complex EEG signal. A particular FFT used is described in more detail in "Computers in the Brain, Part 2" by S. A. Ciarcia, Byte, July 1988, pp. 289-296. If enough data is not available, the game continues in the current mode and the data continues to accumulate. When enough data is available to perform an FFT, the values for the beta activity at electrode site $S_1$, the alpha activity at electrode site $S_2$ and the theta activity at electrode site $S_3$ are available for computation. $S_1$, $S_2$, and $S_3$ may be the same site or different sites. A computation is then performed to derive a numerical value indicative of attention. For example, the previously discussed index may be used, i.e., $$(K_1*bS_1)/(K_2*aS_2+K_3*tS_3).$$

As noted before this index has greater values when a subject is attentive and exhibits high beta activity. Any other suitable index which is attention/beta activity-sensitive may be employed. For example, the attached program employs a simple ratio of beta activity to theta activity. FIG. 5 depicts numerical value of awareness entitled "The Force" as $(beta_1+beta_2)/(theta+alpha)$. If this relationship is used, an additional electrode site is identified as discussed above for $beta_2$ activity. Once calculated, the attention value is displayed on the video screen 10. The attention value is displayed as a bar graph 14 and numerical value display 16.

In addition to the positive reinforcement of a visual display of attention level, the present invention provides an effect on the game. Specifically, a delta time value is calculated based on the numerical value indicative of attention. As this attention value increases, the delta time, or dTime, decreases. This decreased value of dTime causes the subjective time of the game, i.e., the relative speed of the enemy ships, to slow down, thus making it much easier for the subject to hit the ships and score points. The subject is thus encouraged to maintain this attention level since the game is easier and his scores are improved. A minimum threshold should be placed on dTime to avoid a lethargic game which would undesirably disengage the subject's attention. Likewise, as the attention value decreases, the relative speed of the depicted objects increases, thereby making the game more difficult and discouraging lapses in attention. The objective time of the game continues unaffected by the attention level. For example, see the subroutine labeled "Master Control Loop" in the attached program wherein dTime is decreased as the attention level increases and visa versa.

In addition to correlating the subjective time of the game with the attention level, the present invention alters other parameters. For example, the normal operations of the selected video game introduces an effect termed jitter or evasiveness which results in the position of the enemy target and ships constantly changing in an unpredictable, seemingly erratic pattern, thereby increasing the difficulty of the game. This jitter effect is conventionally achieved by, e.g., calculating new x and y positions for the graphic images using a randomly generated incremental change from the previous x and y values establishing position at a particular time. The present invention inversely relates the degree of this incremental change to the attention level, i.e., the evasiveness decreases as the attention level increases and visa versa. For example, see the subroutine labeled "Display Death Star" in the attached program wherein the variables m and n designate x and y coordinates whose respective ranges of changes are reduced as attention increases.

The inverse correlation of desired attention levels with the game difficulty occurs as close to real time as hardware and software operating parameters permit. By quickly adjusting the difficulty level with a sensed change in EEG activity at the selected sites, the present invention permits the subject to better identify the desired and undesired levels of attention as the game difficulty changes. Preferably, this adjustment is continuously performed by the method of the invention as the awareness level changes, rather than at specified incremental awareness levels.

The subject is thus encouraged to maintain appropriate levels of attention in order to succeed in playing the game. A personalized data file for each subject is stored in an appropriate format in the computer memory ROM or appropriate media and should include such information as initial battery, scores, electrode sites for selected mental states, average attention level throughout each game, etc. in addition to standard subject biographical information.

The present invention provides feedback to the subject to encourage him to raise and maintain his attention level for longer periods of time by inversely correlating attention level with the difficulty of the game. The excitement of a video game will usually interest the subject much more than conventional numerical or graphic displays of attention levels.

Many improvements, modifications and substitutions will be apparent to the skilled artisan without departing from the spirit and scope of the present invention as described herein and defined in the following claims.

We claim:

1. A method of modifying a video game to encourage increased attention levels in a subject, the video game comprising a display which depicts objects and a difficulty adjuster which adjusts a level of difficulty for the subject to interact with the objects depicted on the display, the modification method comprising the steps of:

measuring electrical activity in the brain of the subject over time to obtain at least one signal having a value indicative of the level of attention in the subject;

displaying a symbol representing the value indicative of the level of attention on the display of the video game for viewing by the subject; and increasing the level of difficulty via the difficulty adjuster for the subject to interact with the objects depicted on the display as the value indicative of the level of attention decreases and decreasing the level of difficulty via the difficulty adjuster for the subject to interact with the objects depicted on the display as the value indicative of the level of attention increases over time, whereby the value indicative of the level of attention in the subject is inversely related to the level of difficulty for the subject to interact with the depicted objects.

2. The method according to claim 1, wherein said measuring step comprises measuring beta activity (approximately 13–20 Hz) to obtain the at least one signal indicative of the level of attention in the subject.

3. The method according to claim 1, wherein said measuring step comprises measuring a first signal indicative of beta activity (approximately 13–20 Hz) and a second signal indicative of theta activity (approximately 4–8 Hz); and further comprising defining the value indicative of the level of attention in the subject as a ratio of the first beta signal to the second theta signal prior to said displaying step and said increasing and decreasing steps.

4. The method according to claim 1, wherein said measuring step comprises measuring a first signal indicative of $beta_1$ activity (approximately 13–20 Hz), a second signal indicative of $beta_2$ activity (approximately 20–40 Hz), a third signal indicative of alpha activity (approximately 8–13 Hz) and a fourth signal indicative of theta activity (approximately 4–8 Hz); and further comprising defining the value indicative of the level of attention in the subject as the ratio of the sum of the first signal indicative of $beta_1$ activity and the second signal indicative of $beta_2$ activity to the sum of the third signal indicative of alpha activity and the fourth signal indicative of theta activity prior to said displaying step and said increasing and decreasing steps.

5. The method according to claim 1, wherein said measuring step comprises measuring a first signal indicative of $beta_1$ activity (approximately 13–20 Hz), a second signal indicative of alpha activity (approximately 8–13 Hz), and a third signal indicative of theta activity (approximately 4–8 Hz); and further comprising defining the value indicative of the level of attention in the subject as the ratio of first signal indicative of beta activity to the sum of the second signal indicative of alpha activity and the third signal indicative of theta activity prior to said displaying step and said increasing and decreasing steps.

6. The method according to claim 5, wherein said defining step further comprises weighting the values of the first, second and third signals in accord with the relative signal activity of each signal to the total activity of the three signals.

7. The method according to claim 1, wherein the difficulty adjuster increases the level of difficulty by a particular amount, and further comprising increasing the particular amount of the increased level of difficulty as the value indicative of the level of attention decreases and decreasing the particular amount of the increased level of difficulty as the value indicative of the level of attention increases.

8. The method according to claim 2, wherein the difficulty adjuster increases the level of difficulty by a particular amount, and further comprising increasing the particular amount of the increased level of difficulty as the value indicative of the level of attention decreases and decreasing the particular amount of the increased level of difficulty as the value indicative of the level of attention increases.

9. The method according to claim 3, wherein the difficulty adjuster increases the level of difficulty by a particular amount, and further comprising increasing the particular amount of the increased level of difficulty as the value indicative of the level of attention decreases and decreasing the particular amount of the increased level of difficulty as the value indicative of the level of attention increases.

10. The method according to claim 4, wherein the difficulty adjuster increases the level of difficulty by a particular amount, and further comprising increasing the particular amount of the increased level of difficulty as the value indicative of the level of attention decreases and decreasing the particular amount of the increased level of difficulty as the value indicative of the level of attention increases.

11. The method according to claim 5, wherein the difficulty adjuster increases the level of difficulty by a particular amount, and further comprising increasing the particular amount of the increased level of difficulty as the value indicative of the level of attention decreases and decreasing the particular amount of the increased level of difficulty as the value indicative of the level of attention increases.

12. The method according to claim 6, wherein the difficulty adjuster increases the level of difficulty by a particular amount, and further comprising increasing the particular amount of the increased level of difficulty as the value indicative of the level of attention decreases and decreasing the particular amount of the increased level of difficulty as the value indicative of the level of attention increases.

13. The method according to claim 1, wherein the difficulty adjuster increases a relative speed of the objects depicted on the display by a particular amount at a particular time, whereby the level of difficulty increases as the relative speed of the depicted objects increases; and further comprising increasing the particular amount of increased relative speed of the depicted objects at a particular time as the value indicative of the level of attention decreases and decreasing the particular amount of increased relative speed at a particular time as the value indicative of the level of attention increases.

14. The method according to claim 1, wherein the difficulty adjuster increases a defined range of possible positions for a depicted object by a particular amount at a particular time, whereby the level of difficulty increases as the range increases; and further comprising increasing the particular amount of the increased defined range of possible positions at a particular time as the value indicative of the level of attention decreases and decreasing the particular amount of the increased defined range of possible positions at a particular time as the value indicative of the level of attention increases.

* * * * *